United States Patent [19]

Maignan et al.

[11] Patent Number: 5,034,387
[45] Date of Patent: Jul. 23, 1991

[54] 2,4-TRIAMINOPYRIMIDINE-3-OXIDES USED IN COSMETIC AND PHARMACEUTICAL COMPOSITIONS

[75] Inventors: Jean Maignan, Tremblay-les-Gonesse; Serge Restle, Aulnay-sous-Bois; Gerard Lang, Saint-Gratien, all of France

[73] Assignee: L'Oreal, Paris, France

[21] Appl. No.: 487,217

[22] Filed: Feb. 21, 1990

Related U.S. Application Data

[62] Division of Ser. No. 225,849, Jul. 29, 1988, Pat. No. 4,945,093.

[30] Foreign Application Priority Data

Jul. 31, 1987 [LU] Luxembourg .......................... 86959

[51] Int. Cl.$^5$ .................. A61K 31/505; A61K 31/535
[52] U.S. Cl. .................................. 514/235.8; 514/256; 514/880
[58] Field of Search ...................... 514/235.8, 256, 880

[56] References Cited

U.S. PATENT DOCUMENTS

| | | | |
|---|---|---|---|
| 3,461,461 | 8/1969 | Anthony et al. ...................... | 544/323 |
| 4,139,619 | 2/1979 | Chidsey, III ........................ | 544/323 |
| 4,596,812 | 6/1986 | Chidsey, III et al. .............. | 544/323 |
| 4,945,093 | 7/1940 | Maignan et al. .................... | 514/235.8 |

FOREIGN PATENT DOCUMENTS

86/00616  1/1986  PCT Int'l Appl. ................. 544/323

*Primary Examiner*—Leonard Schenkman

*Attorney, Agent, or Firm*—Fleit, Jacobson, Cohn, Price, Holman & Stern

[57] ABSTRACT

A compound having formula:

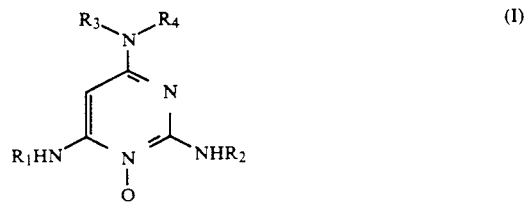

is described, where
  $R_3$ and $R_4$ may be identical or different and represent a hydrogen atom, alkyl, alkenyl, cycloalkyl;
  or $R_3$ and $R_4$ represent aryl aralkyl;
  or $R_3$ and $R_4$ together with the nitrogen atom linked thereto form a heterocycle;
  $R_1$ and/or $R_2$, independent of each other, represent hydrogen or carbanoyl having formula:

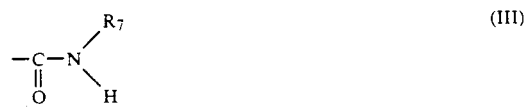

where $R_7$ represents alkyl, alkenyl, cycloalkyl, aryl or aralkyl.

The compounds of formula (I) can be used in cosmetic or pharmaceutical compositions for the cosmetic treatment of hair, the treatment of alopecia, and also for the treatment of desquamating dermatitis.

5 Claims, No Drawings

2,4-TRIAMINOPYRIMIDINE-3-OXIDES USED IN COSMETIC AND PHARMACEUTICAL COMPOSITIONS

This is a divisional of application Ser. No. 225,849 filed July 29, 1988 now U.S. Pat. No. 4,945,093.

BACKGROUND OF THE INVENTION

1. Field of the Invention

The present invention relates to novel derivatives of pyrimidine-3-oxide, to their preparation and to cosmetic or pharmaceutical compositions especially intended for topical application.

2. Description of the Prior Art 6-piperidino-2,4-diaminopyrimidine-3-oxide or "Minoxidil" is already known in the art for both its antihypertensive properties and its use in the treatment of hair loss, alopecia, desquamative dermatitis, etc.

The applicant has discovered novel derivatives of pyrimidine-3-oxide which are 2- and/or 4-position mono- or diureas of 2,4,6-triaminopyrimidine-3-oxide.

These products are particularly effective for hair regrowth and may be used for treatment of illnesses causing baldness, such as alopecia, hair loss and desquamative dermatitis.

One object of the invention is therefore novel derivatives of 2,4,6-triaminopyrimidine-3-oxide.

Another object of the invention is a process for their preparation.

The invention also concerns cosmetic and/or pharmaceutical compositions using these compounds.

Further objects of the invention will become apparent from the following description and examples.

SUMMARY OF THE INVENTION

In one aspect the invention consists in a compound having the formula:

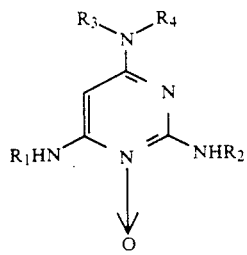

where:

R$_3$ and R$_4$ may be identical or different and represent a hydrogen atom, a linear or branched C$_1$-C$_{18}$ alkyl group, an alkenyl group having 2 to 18 carbon atoms, a 5 to 8 carbon atom cycloalkyl group which may have one or more of the following substituents:
  a low alkyl group,
  an alkyl, alkenyl or cycloalkyl group which may itself have one or more substituent hydroxyl groups,
or R$_3$ and/or R$_4$ may represent an aryl group or an aralkyl group corresponding to the formula:

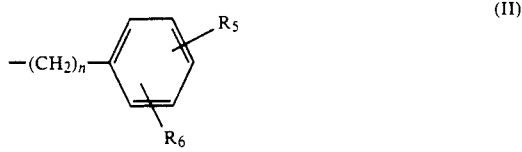

where:
n can take any value from 0 to 4 and/or
R$_5$ and/or R$_6$, independent of each other, represent a hydrogen atom, a C$_1$ to C$_6$ low alkyl group, a nitro group, an hydroxyl group, an alkoxy group, a halogen atom or a carboxy group as well as the salts, esters and amides of the latter groups,
or R$_3$ and R$_4$ may, together with the nitrogen atom linked thereto, form a 3 to 7 carbon atom heterocycle;
R$_1$ and/or R$_2$, independent of each other, represent a hydrogen atom or a carbamoyl group having formula:

providing the R$_1$ and R$_2$ do not simultaneously represent a hydrogen atom, where R$_7$ represents a linear or branched C$_1$ to C$_{18}$ alkyl group, a C$_2$-C$_{18}$ alkenyl group or a C$_5$-C$_8$ cycloalkyl group or an aryl group or an aralkyl group corresponding to said formula (II); and its tautomeric forms having formulae:

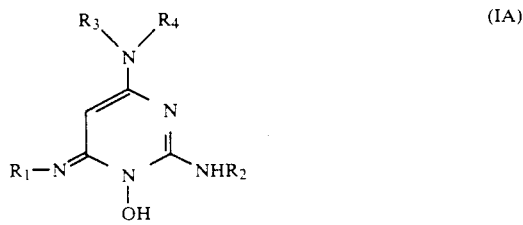

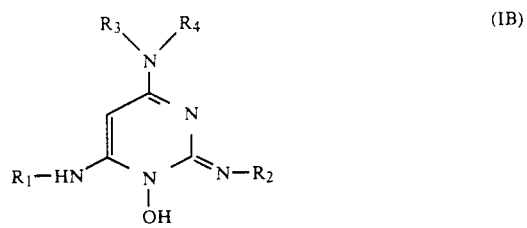

The tautomeric forms (I), (IA) and (IB) can, of course, be present in the mixture in varying proportions. One form may be dominant depending on the nature of the R$_3$, R$_4$, R$_1$ and R$_2$ substituents or the solvent.

According to the invention, the C$_1$-C$_{18}$ alkyl groups are preferably selected from: methyl, ethyl, propyl, 2-ethylhexyl, octyl, dodecyl, hexadecyl and octadecyl groups.

"Low alkyl group" means a group having 1 to 6 carbon atoms, particularly methyl, ethyl, isopropyl, butyl and tertiary butyl groups. Particularly preferred alkenyl groups are allyl, butenyl, hexenyl, dodecenyl, hexadecenyl and octadecenyl.

Particularly preferred aryl or aralkyl groups are: phenyl, 4-toluyl, 2-nitrophenyl, 4-nitrophenyl, 4-fluorphenyl, 4-chlorophenyl, 2-carboxyphenyl, 4-carboxyphenyl, 4-hydroxyphenyl, benzyl and phenethyl.

"Heterocycle" preferably includes the following groups: morpholino, piperidino, pyrrolidino, piperazino, or 4'-N-alkylpiperazino where the alkyl group in the 4' position preferably contains 1 to 6 carbon atoms and one may be substituted with an hydroxyl group.

"Halogen atom" preferably means chlorine or fluorine.

Particularly preferred compounds are those in which $R_3$ and $R_4$, together with the nitrogen atom linked thereto, form a piperidino group, and $R_1$ and/or $R_2$ represent the group

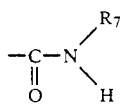

where $R_7$ represents a low alkyl group in particular butyl, $C_5$-$C_8$ cycloalkyl (particularly cyclohexyl), aryl or aralkyl (particularly toluyl).

In another aspect the invention consists in a process for the preparation of a compound having the formula:

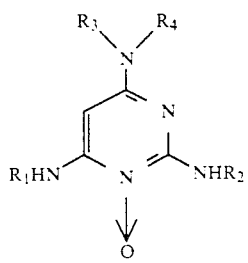

(I)

where:
$R_3$ and $R_4$ may be identical of different and represent a hydrogen atom, a linear or branched $C_1$-$C_{18}$ alkyl group, an alkenyl group having 2 to 18 carbon atoms, a cycloalkyl group having 5 to 8 carbon atoms which may have one or more of the following substituents:
a low alkyl group,
an alkyl, alkenyl or cycloalkyl group which may itself have one or more substituent hydroxyl groups,
or $R_3$ and/or $R_4$ may represent an aryl group or an aralkyl group corresponding to the formula:

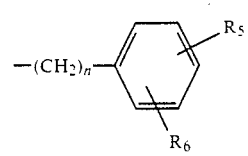

(II)

where:
n can take any value from 0 to 4, and
$R_5$ and/or $R_6$, independent of each other, represent a hydrogen atom, a $C_1$ to $C_6$ low alkyl group, a nitro group, an hydroxyl group, an alkoxy group, a halogen atom or a carboxyl group as well as the salts, esters and amides of the latter groups,
or $R_3$ and $R_4$ may, together with the nitrogen atom linked thereto, form a 3 to 7 carbon atom heterocycle;

$R_1$ and/or $R_2$, independent of each other, represent a hydrogen atom or a carbamoyl group having formula:

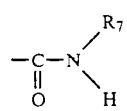

(III)

providing that $R_1$ and $R_2$ do not simultaneously represent a hydrogen atom, where $R_7$ represents a linear or branched $C_1$ to $C_{18}$ alkyl group, a $C_2$-$C_{18}$ alkenyl group or a $C_5$-$C_8$ cycloalkyl group or an aryl group or an aralkyl group corresponding to said formula (II); and its tautomeric forms having formulae:

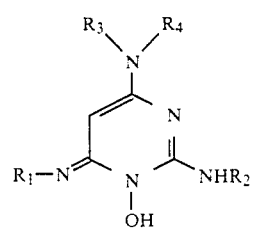

(IA)

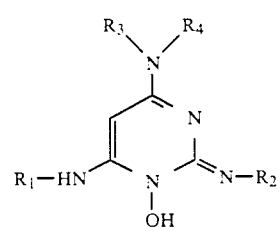

(IB)

in particular a compound having the formula (VIII):

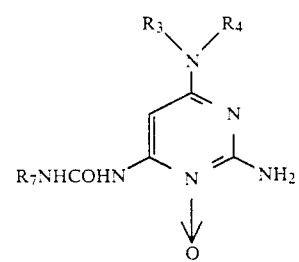

(VIII)

or (XIII):

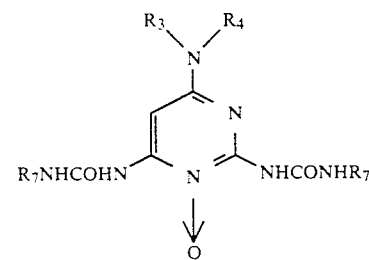

(XIII)

said process comprising: treating 6-chloro-2,4-diamino pyrimidine with an isocyanate having formula $R_7-N=C=O$ in a polar aprotic organic solvent, oxidizing the derivatives produced and treating with an amine having formula:

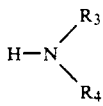

In a further aspect the invention consists in a process for the preparation of a compound having the formula:

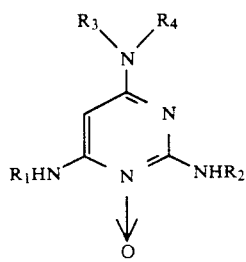
(I)

where:
R$_3$ and R$_4$ may be identical or different and represent a hydrogen atom, a linear or branched C$_1$-C$_8$ alkyl group, an alkenyl group having 2 to 18 carbon atoms, a cycloalkyl group having 5 to 8 carbon atoms which may have one or more of the following substituents:
a low alkyl group,
an alkyl, alkenyl or cycloalkyl group which may itself have one or more substituent hydroxyl groups,
or R$_3$ and/or R$_4$ may represent an aryl group or an aralkyl group corresponding to the formula:

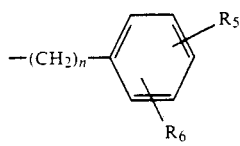
(II)

where:
n can take any value from 0 to 4, and
R$_5$ and/or R$_6$, independent of each other, represent a hydrogen atom, a C$_1$ to C$_6$ low alkyl group, a nitro group, an hydroxyl group, an alkoxy group, a halogen atom or a carboxyl group as well as the salts, esters and amides of the latter groups,
or R$_3$ or R$_4$ may, together with the nitrogen atom linked thereto, form a 3 to 7 carbon atom heterocycle;
R$_1$ and/or R$_2$, independent of each other, represent a hydrogen atom or a carbamoyl group having formula:

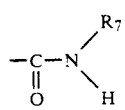
(III)

providing that R$_1$ and R$_2$ do not simultaneously represent a hydrogen atom, where R$_7$ represents a linear or branched C$_1$ to C$_{18}$ alkyl group, a C$_2$-C$_{18}$ alkenyl group or a C$_5$-C$_8$ cycloalkyl group or an aryl group or an aralkyl group corresponding to said formula (II); and its tautomeric forms having formulae:

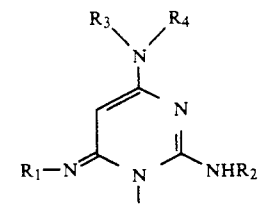
(IA)

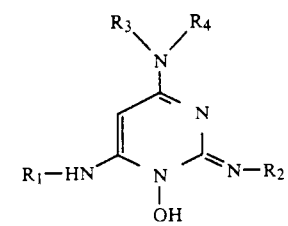
(IB)

in particular a compound having formula (XI):

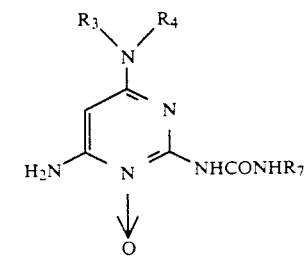
(XI)

said process comprising: treating 6-chloro-2,4-diamino pyrimidine with an isocyanate having formula R$_7$—N=C=O in tetrahydrofuran, or treating 6-hydroxy-2,4-diaminopyrimidine with said isocyanate in N-methyl pyrrolidone to form a condensation product and transforming said condensation product into a corresponding tosylate, oxidizing said tosylate or derivative from the condensation of said isocyanate with said 6-chloro-2,4-diaminopyrimidine to the corresponding N-oxide, and reacting said N-oxide with an amine of formula:

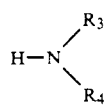

In a still further aspect the invention consists in a process for the preparation of a compound having the formula:

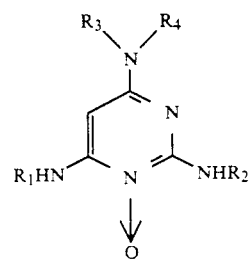
(I)

where:

R₃ and R₄ may be identical or different and represent a hydrogen atom, a linear or branched $C_1$-$C_{18}$ alkyl group, an alkenyl group having 2 to 18 carbon atoms, a cycloalkyl group having 5 to 8 carbon atoms which may have one or more of the following substituents:

a low alkyl group, an alkyl, alkenyl or cycloalkyl group which may itself have one or more substituent hydroxyl groups, or R₃ and/or R₄ may represent an aryl group or an aralkyl group corresponding to the formula:

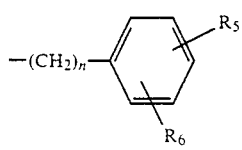
(II)

where:

n can take any value from 0 to 4, and

R₅ and/or R₆, independent of each other, represent a hydrogen atom, a $C_1$ to $C_6$ low alkyl group, a nitro group, an hydroxyl group, an alkoxy group, a halogen atom or a carboxyl group as well as the salts, esters and amides of the latter groups, or R₃ and R₄ may, together with the nitrogen atom linked thereto, form a 3 to 7 carbon atom heterocycle;

R₁ and/or R₂, independent of each other, represent a hydrogen atom or a carbamoyl group having formula:

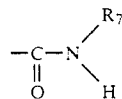
(III)

providing that R₁ and R₂ do not simultaneously represent a hydrogen atom, where R₇ represents a linear or branched $C_1$ to $C_{18}$ alkyl group, a $C_2$-$C_{18}$ alkenyl group or a $C_5$-$C_8$ cycloalkyl group or an aryl group or an aralkyl group corresponding to said formula (II); and its tautomeric forms having formulae:

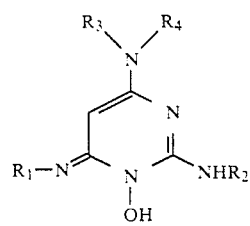
(IA)

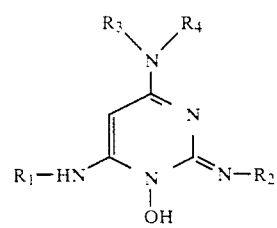
(IB)

particularly of compounds having formulae (XIV), (XV) and (XVI):

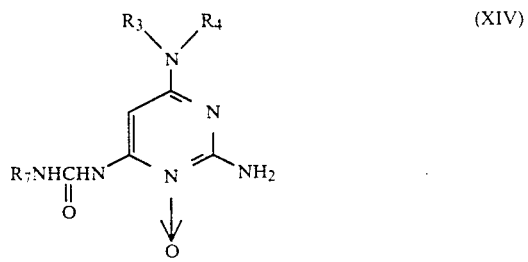
(XIV)

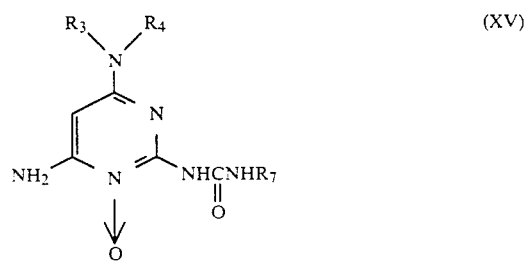
(XV)

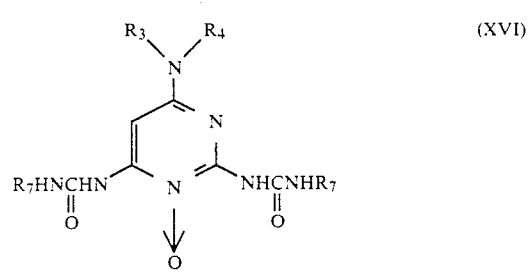
(XVI)

said process comprising: treating a 2,4,6-triamino pyrimidine-3-oxide with an isocyanate having formula R₇—N=C=O where the 6-position amino group represents the group

in a polar aprotic solvent at a temperature of between 20° and 100° C.

In a different aspect the invention consists in a cosmetic or pharmaceutical composition containing, disposed in a support appropriate for topical application, at least one compound having the formula:

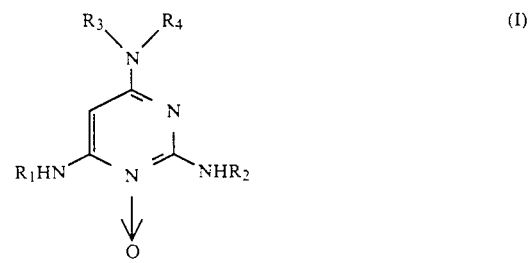
(I)

where:

R₃ and R₄ may be identical or different and represent a hydrogen atom, a linear or branched $C_1$-$C_{18}$ alkyl group, an alkenyl group having 2 to 18 carbon atoms, a cycloalkyl group having 5 to 8 carbon atoms which may have one or more of the following substituents:
a low alkyl group,
an alkyl, alkenyl or cycloalkyl group which may itself have one or more substituent hydroxyl groups,
or $R_3$ and/or $R_4$ may represent an aryl group or an aralkyl group corresponding to the formula:

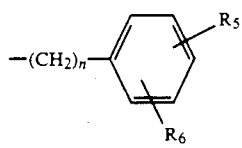
(II)

where:
n can take any value from 0 to 4, and
$R_5$ and/or $R_6$, independent of each other, represent a hydrogen atom, a $C_1$ to $C_6$ low alkyl group, a nitro group, an hydroxyl group, an alkoxy group, a halogen atom or a carboxyl group as well as the salts, esters and amides of the latter groups,
or $R_3$ and $R_4$ may, together with the nitrogen atom linked thereto, form a 3 to 7 carbon atom heterocycle;
$R_1$ and/or $R_2$, independent of each other, represent a hydrogen atom or a carbamoyl group having formula:

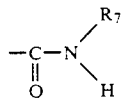
(III)

providing that $R_1$ and $R_2$ do not simultaneously represent a hydrogen atom, where $R_7$ represents a linear or branched $C_1$ to $C_{18}$ alkyl group, a $C_2$-$C_{18}$ alkenyl group or a $C_5$-$C_8$ cycloalkyl group or an aryl group or an aralkyl group corresponding to said formula (II); and its tautomeric forms having formulae:

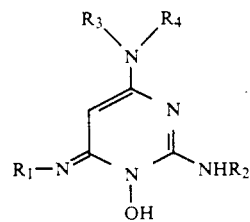
(IA)

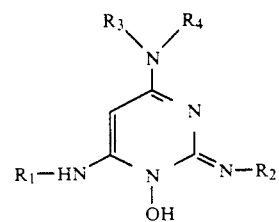
(IB)

In another aspect the invention consists in a process for the cosmetic treatment of hair whereby there is applied to the scalp at least one cosmetic or pharmaceutical composition containing, disposed in a support appropriate for topical application, at least one compound having the formula:

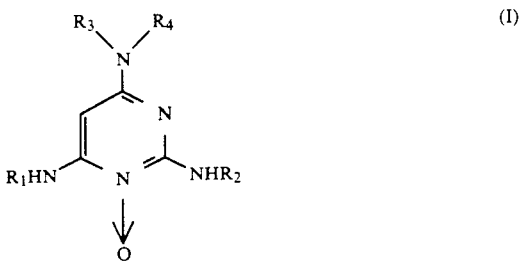
(I)

where:
$R_3$ and $R_4$ may be identical or different and represent a hydrogen atom, a linear or branched $C_1$-$C_{18}$ alkyl group, an alkenyl group having 2 to 18 carbon atoms, a cycloalkyl group having 5 to 8 carbon atoms which may have one or more of the following substituents:
a low alkyl group,
an alkyl, alkenyl or cycloalkyl group which may itself have one or more substituent hydroxyl groups,
or $R_3$ and/or $R_4$ may represent an aryl group or an aralkyl group corresponding to the formula:

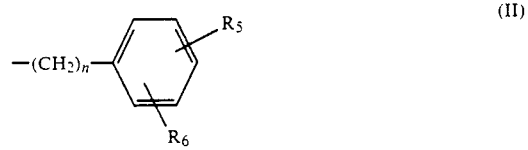
(II)

where:
n can take any value from 0 to 4, and
$R_5$ and/or $R_6$, independent of each other, represent a hydrogen atom, a $C_1$ to $C_6$ low alkyl group, a nitro group, an hydroxyl group, an alkoxy group, a halogen atom or a carboxyl group as well as the salts, esters and amides of the latter groups,
or $R_3$ and $R_4$ may, together with the nitrogen atom linked thereto, form a 3 to 7 carbon atom heterocycle;
$R_1$ and/or $R_2$, independent of each other, represent a hydrogen atom or a carbamoyl group having formula:

(III)

providing that $R_1$ and $R_2$ do not simultaneously represent a hydrogen atom, where $R_7$ represents a linear or branched $C_1$ to $C_{18}$ alkyl group, a $C_2$-$C_{18}$ alkenyl group or a $C_5$-$C_8$ cycloalkyl group or an aryl group or an aralkyl group corresponding to said formula (II); and its tautomeric forms having formulae:

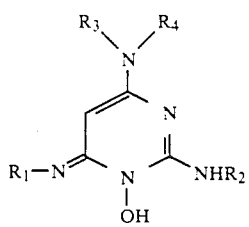
(IA)

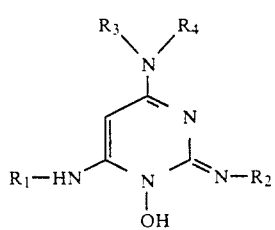
(IB)

wherein the composition takes the form of an ointment, tincture, cream, pomade, powder, sticking plaster, impregnated pad, solution, emulsion, lotion, gel, spray or anhydrous or aqueous suspension, wherein the compound having formula I is present in concentrations comprised between 0.1 and 10% by weight with respect to the total composition weight, and particularly between 0.2 and 5% by weight.

In a further aspect the invention consists of use of a compound having the formula:

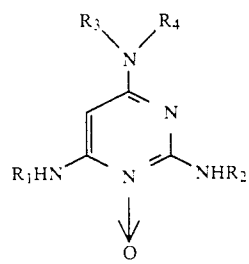
(I)

where:
R$_3$ and R$_4$ may be identical or different and represent a hydrogen atom, a linear or branched C$_1$-C$_{18}$ alkyl group, an alkenyl group having 2 to 18 carbon atoms, a cycloalkyl group having 5 to 8 carbon atoms which may have one or more of the following substituents:
a low alkyl group,
an alkyl, alkenyl or cycloalkyl group which may itself have one or more substituent hydroxyl groups,
or R$_3$ and/or R$_4$ may represent an aryl group or an aralkyl group corresponding to the formula:

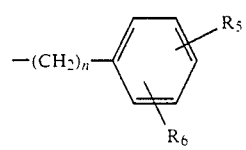
(II)

where:
n can take any value from 0 to 4, and
R$_5$ and/or R$_6$, independent of each other, represent a hydrogen atom, a C$_1$ to C$_6$ low alkyl group, a nitro group, an hydroxyl group, an alkoxy group, a halogen atom or a carboxyl group as well as the salts, esters and amides of the latter groups, or R$_3$ and R$_4$ may, together with the nitrogen atom linked thereto, form a 3 to 7 carbon atom heterocycle;

R$_1$ and/or R$_2$, independent of each other, represent a hydrogen atom or a carbamoyl group having formula:

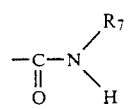
(III)

providing that R$_1$ and R$_2$ do not simultaneously represent a hydrogen atom, where R$_7$ represents a linear or branched C$_1$ to C$_{18}$ alkyl group, a C$_2$-C$_{18}$ alkenyl group or a C$_5$-C$_8$ cycloalkyl group or an aryl group or an aralkyl group corresponding to said formula (II); and its tautomeric forms having formulae:

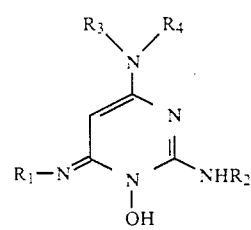
(IA)

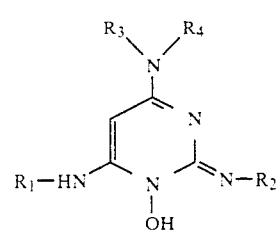
(IB)

in the preparation of a medicament for the treatment of alopecia, hair loss or desquamating dermatitis.

The inventive process can be illustrated by the following reaction schemes:

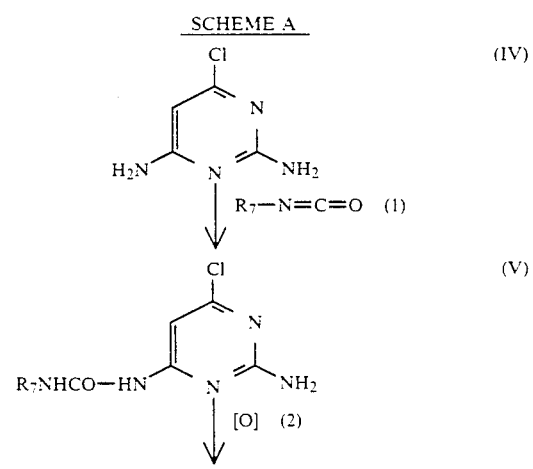

SCHEME A

-continued

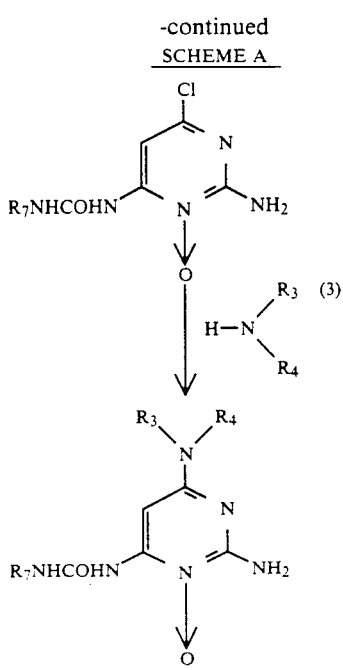

SCHEME B

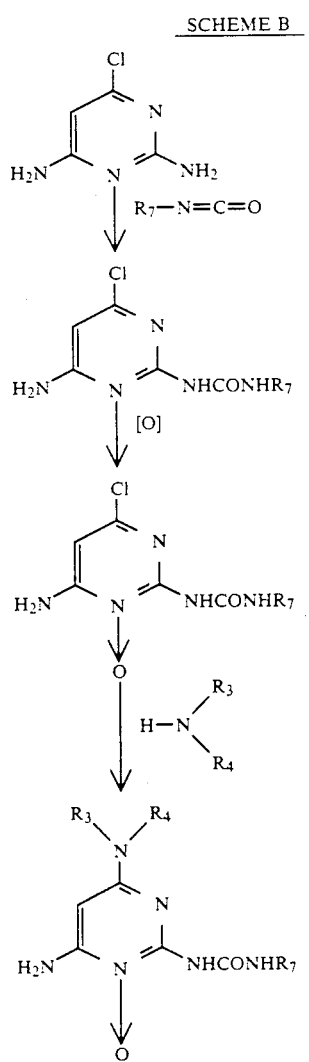

SCHEME A

Stage 1 consists in treating commercially available 6-chloro-2,4-diaminopyrimidine having formula IV with an isocyanate having formula:

$$R_7-N=C=O$$

where $R_7$ has the meanings given above.

The reaction is carried out in a polar aprotic organic solvent such as dimethylsulfoxide (DMSO), dimethylformamide (DMF) or N-methylpyrrolidone. In an excess of isocyanate the urea derivative corresponding to formula (V) is surprisingly obtained as the predominating product.

Prolonging the reaction time and keeping product (V) in an excess of isocyanate can synthesize a diurea derivative having formula (VI):

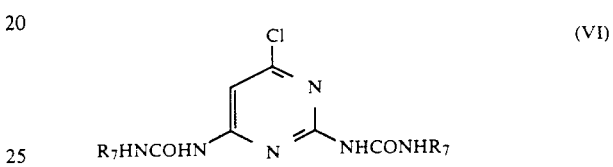

whose 2- and 4-position amino groups have been transformed into the corresponding urea.

In stage 2, compound (V) is oxidized to a corresponding pyrimidine 3-oxide having formula (VII), either by the action of metachloroperbenzoic acid or by using peracids formed in situ by the action of oxygenated water on an organic acid.

Particularly good results are obtained using a heterogeneous phase, in a mixture of a chlorinated solvent such as dichloromethane or an ether such as dioxan in the presence of about 5 to 30%, preferably 10%, formic acid, and containing in particular a compound having formula (V) to which is added a slight excess of oxygenated water. The reaction is preferably carried out at a temperature of between 0° and 70° C. The oxidation reaction is selective and very high yields of pyrimidine 3-oxides can be isolated either by eliminating the chlorinated solvent by vacuum evaporation, pouring the mixture into water and isolating the product by filtration, or, given the nature of the $R_7$ group, by direct filtration out of the reaction medium. These products have sufficient purity to enable them to be directly treated in a third stage.

In stage 3, the products obtained from the previous stages may be directly used and treated with an amine having formula:

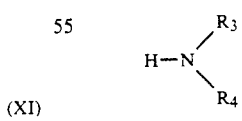

This chlorine displacement reaction is effected depending on the basicity of the amine:

either by using it in excess, thereby employing it both as solvent and reactant; or by using an organic solvent with an amine in a slight excess of 1.5 to 5 equivalents.

This reaction is carried out at a temperature compatible with the boiling point of the amine and between 0° and 150° C., but preferably at about 70° C. In this way good yields of pyrimidine oxides of formula (VIII) are obtained.

Stages 2 and 3 are followed in order to transform the diureas having formula (VI) into product (XIII):

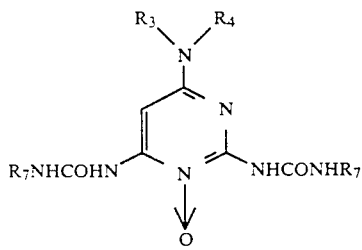

SCHEME B

Using a different aprotic solvent such as tetrahydrofuran (THF) during the first stage of the synthesis, surprisingly the urea having formula (V) is not obtained even in small amounts, but rather the 6-chloro-2-N-carbamoylamino-4-aminopyrimidine having formula (IX) according to scheme B.

This product is then oxidized as above under the same operational conditions into the corresponding oxide. Finally, by reaction with an amine

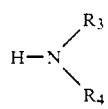

a product having formula (XI) is obtained.

According to a further embodiment, compounds having formula (XI) may be obtained as shown in scheme C below by treating 6-hydroxy-2,4-diaminopyrimidine (IVb) with an isocyanate $R_7-N=C=O$ in an aprotic solvent such as N-methylpyrrolidone to give a urea having formula (IXb). Reaction of the latter with tosyl chloride produces the corresponding tosylate (IXc).

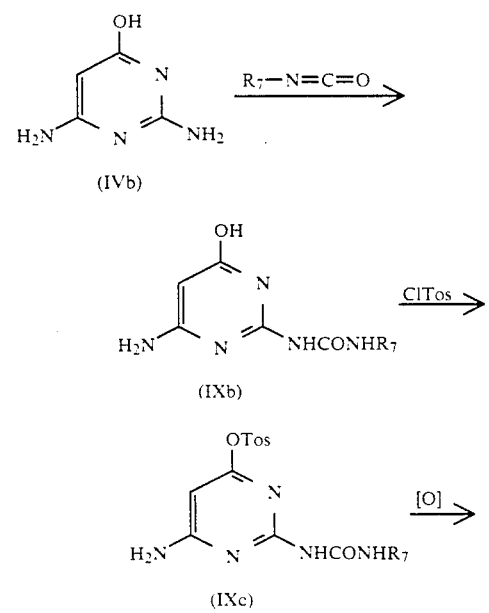

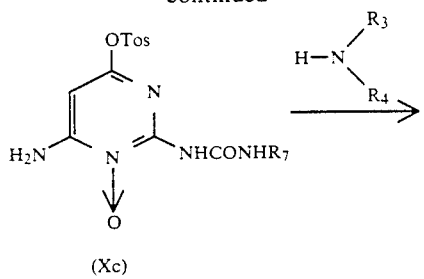

SCHEME C

Treatment of the tosylate with an organic peracid produces the corresponding N-oxide (Xc) which, on reaction with an excess of the amine

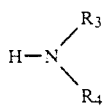

produces the inventive compound having formula (XI).

According to a third embodiment, compounds according to the invention may also be prepared from 2,4,6-triaminopyrimidine-3-oxide by treatment with an isocyanate, thereby substituting the 6-position amino group as indicated above.

2,4,6-triaminopyrimidine-3-oxides are themselves known in the art and may be prepared according to the process defined in U.S. Pat. No. 3,910,928.

The isocyanate is reacted with the 2,4,6-triaminopyrimidine-3-oxide in accordance with Scheme D below, in a polar aprotic solvent such as DMSO, DMF, THF, dimethylacetamide etc at a temperature of between 20° C. and 100° C. These temperatures must, of course, be compatible with the boiling point of the isocyanate.

SCHEME D

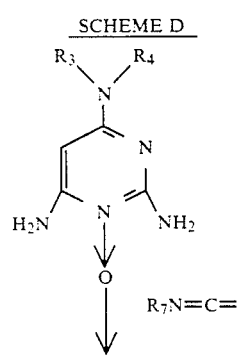

-continued
SCHEME D

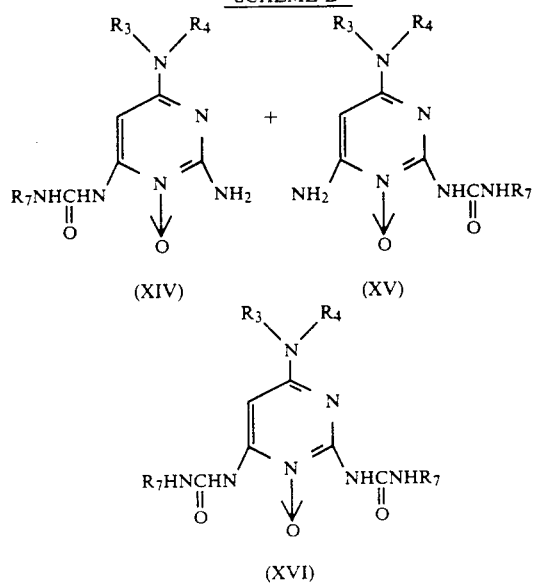

Generally speaking, although an excess of isocyanate is used, synthesis of monoureas having formula (XIV) or (XV) is much faster than that of diureas having formula (XVI).

Thus, according to the invention good yields of monocondensation derivatives (XIV) or (XV) can be obtained. As a general rule, a mixture of the two products (XIV) and (XV) is always obtained which contains a larger or smaller quantity of the diurea (XVI), depending on the reaction temperature and the quantity of isocyanate used.

Selecting an appropriate solvent surprisingly produces a great predominance of one of the products (XIV) or (XV). Thus, carrying out the reaction in DMSO produces compound (XIV) in the considerable majority.

Diureas having formula (XVI) whose urea functions are identical can be prepared, as indicated above, from products (XIV) and (XV).

According to the invention it is also possible to prepare products having formulae (XVII) or (XVIII) having different urea functions:

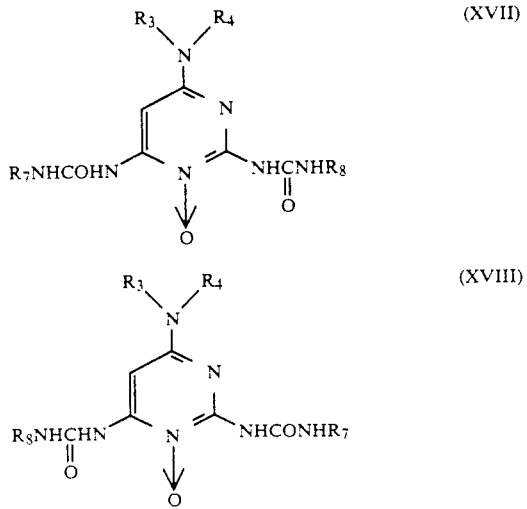

by treatment of monoureas (XIV) or (XV), respectively, with an isocyanate having formula:

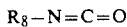

$$R_8-N=C=O$$

where $R_8$ may be identical to or different from $R_7$ and has the same meaning as $R_7$.

Reciprocally, it may be advantageous to prepare monoureas (XV) from diureas having formula (XVI) by treating the latter in a basic medium.

Compounds according to the invention can be used in the cosmetics or pharmaceuticals field, particularly for topical applications. The applicant has established that, surprisingly, compounds according to the invention have much less cardiovascular effect than those whose 2- and/or 4-position amino functions are free.

They are also very stable.

Cosmetic or pharmaceutical compositions which constitute a further object of the invention are used particularly for treatment of baldness, particularly alopecia, hair loss, desquamative dermatitis, etc.

These compositions are primarily characterized in that they contain, in an appropriate cosmetic or pharmaceutical support for topical application, at least one compound corresponding to formula I or its tautomeric forms and/or one of its salts, esters or amides.

Compositions according to the invention may comprise any support which is appropriate for topical application and compatible with the active substance. The inventive compounds may be either dispersed or dissolved in the support.

Compositions intended for pharmaceutical use may be in the form of ointments, tinctures, creams, pomades, powders, sticking plasters, impregnated pads, solutions, emulsions, lotions, gels, sprays or suspensions. They may be anhydrous or aqueous depending on the clinical indication.

The compounds are present in these compositions in concentration of between 0.1 and 10% by weight, in particular between 0.2 and 5% by weight.

Cosmetic compositions are particularly intended to be used as lotions, gels, soaps or shampoos and contain at least one compound having formula (I) or one of its salts, esters or amides in a physiologically acceptable support.

Such compositions preferably contain concentrations of compound (I) between 0.01 and 5% by weight, in particular between 0.05 and 3% by weight.

Compositions according to the invention may contain different additives which are normally used in cosmetics or pharmaceuticals and which are inert with respect to the active substance. The following can be mentioned in this respect: hydrating agents such as thiamorpholinone and its derivatives or urea; antiseborrheic agents such as S-carboxymethylcysteine, S-benzylcystamine and its derivatives, thioxolane; hair regrowth agents such as phenytoin (5,5-diphenylimidazole-2,4-dione) or oxapropanium iodide, retinoic acid and its derivatives, compounds described in patent applications EP-A-0 220 118, EP-A-0 232 199, FR-A-2 600 064, FR-A-2 599 031, FR-A-2 601 002, EP-A-0 260 162 and GB-A-2 197 316, anthraline and its derivatives; steroid or non-steroid anti-inflammatory agents; carotenoids and, most particularly, β-carotene, also eicosa-5,8,11,14-tetraynoic and eicosa-5,8,11-triynoic acids, and their esters and amides.

The compositions may also contain conservatives, stabilisers, pH regulators, osmotic pressure modifiers, emulsifiers, UV-A and UV-B filters or antioxidants such as α-tocopherol, butylhydroxyanisole or butylhydroxy toluene.

The invention also provides a process for cosmetic hair treatment consisting in applying at least one composition as defined above to the scalp.

A still further object of the invention is the use of compounds having formula (I) in the preparation of a medicament for the treatment of alopecia, hair loss or desquamative dermatitis.

DESCRIPTION OF THE INVENTION

The following examples are intended to illustrate the invention without in any way limiting its scope.

EXAMPLE I

Synthesis of
N-(6-piperidino-2-amino-3-oxide-4-pyrimidinyl),N'-n-butyl urea 6.5 cm$^3$ or butylisocyanate was added in fractions of 1 cm$^3$ every 3-4 hours to a suspension of 10 g of 6-piperidino-2,4-diaminopyrimidine-3-oxide (Minoxidil) in 75 cm$^3$ DMSO at 50°–60° C.

After the last addition the reaction medium became homogeneous. Heating was maintained for about 2 hours then the solution was poured into about 1 liter of ice water with a little acetic acid added. The desired product crystallized. After neutralization of the aqueous phase the crude reaction medium was filtered and vacuum dried.

The crude reaction medium comprised the desired product plus the dicondensation product.

The two products were isolated using silica gel chromatography (eluent: $CH_2Cl_2$—MeOH—$NH_4OH$).

8.5 g of N-(6-piperidino-2-amino-3-oxide-4-pyrimidinyl),N'n-butylurea were obtained as white crystals melting at 202°–204° C.

| Elemental Analysis: $C_{14}H_{24}N_6O_2$ | | | | |
|---|---|---|---|---|
| | C % | H % | N % | O % |
| Calculated: | 54.50 | 7.80 | 27.27 | 10.38 |
| Found: | 54.36 | 7.80 | 27.20 | 10.51 |

0.500 g of the dicondensation product was also obtained in the form of white crystals, melting at 210° C.

| Elemental Analysis: $C_{19}H_{33}N_7O_3$ | | | | |
|---|---|---|---|---|
| | C % | H % | N % | O % |
| Calculated: | 55.99 | 8.16 | 24.06 | 11.77 |
| Found: | 56.06 | 8.19 | 24.05 | 11.90 |

EXAMPLE II

Synthesis of
N,N''-(6-piperidino-3-oxide-2,4-pyrimidinyl) bis (N'-n-butyl)urea 1.5 cm$^3$ of n-butylisocyanate was added to a solution of 1 g of N-(6-piperidino-2-amino-3-oxide-4-pyrimidinyl-N -N'-n-butylurea from example 1 in 20 cm$^3$ DMSO at 50°–60° C. The heating was maintained for 4 hours then the solution was poured over ice water and filtered. The product obtained was dried then recrystallized from methanol. 750 mg of a white product was obtained which agreed with the disubstitution product obtained in example 1 and melted at 208°–209° C.

EXAMPLE III

Synthesis of
N-(6-piperidino-2-amino-3-oxide-4-pyrimidinyl),N'-cyclo hexylurea 9.5 cm$^3$ of cyclohexylisocyanate was added in 1 cm$^3$ fractions over 3-4 hours to a suspension of 10 g of 6-piperidino-2-amino-3-oxide in 75 cm$^3$ DMSO at 50°–60° C.

After the final addition the reaction medium was kept at 60°–75° C. for 5-6 hours. Thin layer chromatography was used to confirm that the starting compound had disappeared. The solution was poured over about 1 liter of ice water with a little added acetic acid. The desired produce crystallized out. After neutralization of the aqueous phase the crude reaction medium was filtered and vacuum dried.

The crude reaction medium comprised the desired product and the dicondensation product.

The two products were isolated using silica gel chromatography (eluent: $CH_2Cl_2$—MeOH—$NH_4OH$).

9.6 g of N-(6-piperidino-2-amino-3-oxide-4pyrimidinyl),N'-cyclohexylurea was obtained as white crystals melting at 214°–215° C. following recrystallization from methanol.

| Elemental Analysis: $C_{16}H_{26}N_6O_2$ | | | | |
|---|---|---|---|---|
| | C % | H % | N % | O % |
| Calculated: | 57.46 | 7.83 | 25.13 | 9.56 |
| Found: | 57.10 | 7.77 | 25.43 | 10.20 |

2.5 g of the dicondensation production was obtained as white crystals whose melting point was 219° C.–220° C. following recrystallization from methanol.

| Elemental Analysis: $C_{23}H_{37}N_7O_3$ | | | | |
|---|---|---|---|---|
| | C % | H % | N % | O % |
| Calculated: | 60.10 | 8.11 | 21.33 | 10.44 |
| Found: | 60.63 | 8.35 | 20.95 | 10.40 |

EXAMPLE IV

Synthesis of
N-(6-piperidino-2-amino-3-oxide-4-pyrimidinyl),N'-toluyl urea 1 cm$^3$ of toluylisocyanate was added to a suspension of 1 g of 6-piperidino2,4-diaminopyrimidine-3-oxide in 50 cm$^3$ of DMSO at 50°–60° C.

After heating for 1 hour at 60° C. the reaction medium became homogeneous, then a white precipitate formed.

After hydrolysis, the precipitate obtained was filtered. The crude reaction medium was dried then recrystallized from a mixture of methylpyrrolidone/diisopropyl ether.

500 mg of N-(6-piperidino-2-amino-3-oxide-4-pyrimidinyl,N'-toluylurea was obtained as a white powder melting at 227°–228° C.

The $^1$H NMR, 80 MHz spectrum agreed with the expected structure and the product was HPLC pure.

EXAMPLE V

Synthesis of N-(6-piperidino-2-amino-3-oxide-4-pyrimidinyl,N'-n-butylurea

Stage 1

Preparation of
N-(2-amino-6-chloro-4-pyrimidinyl),N'-n-butylurea 8.6 cm$^3$ of n-butylisocyanate was added to a suspension of 5 g of 4-chloro-2,6-diaminopyrimidine in 50 cm$^3$ of DMSO then heated to 80° C. until the starting compound was shown by TLC to have disappeared.

After hydrolysis of the reaction medium, the product was extracted with ethyl acetate. The organic phase was washed, dried then concentrated under reduced pressure.

5.1 g of product was obtained which was purified by recrystallization from ethyl acetate.

N-(2-amino-6-chloro-4-pyrimidinyl),N'-n-butylurea crystallized in the form of white crystals melting at 227° C.

The $^1$H NMR, 250 MHz spectrum agreed with the expected structure.

Stage 2

Preparation of
N-(2-amino-3-oxide-6-chloro-4-pyrimidinyl),N'-n-butyl urea 2.17 g of metachloroperbenzoic acid was added to a suspension of 2.8 g of N-(2-amino-6-chloro-4-pyrimidinyl),N'-n-butylurea, prepared as above, in a mixture of 100 cm$^3$ alcohol–15 cm$^3$ water.

The reaction temperature was maintained at 20° C. and its progress was monitored using TLC.

Once the starting compound had been consumed, the alcohol was evaporated off under reduced pressure and the residue taken up into water with added sodium bicarbonate.

After half an hour's vigorous agitation of the aqueous phase, the precipitate was filtered, washed with plenty of water and dried.

2.5 g of white crystals were obtained whose melting point was 195°–196° C. and whose $^1$H NMR spectrum agreed with the expected structure.

Stage 3

Preparation of
N-(6-piperidino-2-amino-3-oxide-4-pyrimidinyl)-N'-n-butylurea

A suspension of 1 g of N-(2-amino-3-oxide-b 6-chloro-4-pyrimidinyl),-N'-n-butylurea, prepared as above, in 10 cm$^3$ piperidine was heated for 1 hour at 100° C.

The reaction medium was poured over ice water and the precipitate obtained filtered off, dried and recrystalized from methanol.

0.950 mg of N-(6-piperidino-2-amino-3-oxide-4-pyrimidinyl),N'-n-butylurea conforming to the product obtained in example 1 was obtained.

EXAMPLE VI

Synthesis of N-(6-piperidino-2-amino-3-oxide-4-pyrimidinyl),N'-isopropylurea 4.7 cm$^3$ of isopropylisocyanate in solution in a little DMSO was added dropwise to a suspension of 10 g of 6-piperidino-2,4-diaminopyrimidine-3-oxide in 75 cm$^3$ of DMSO at 50°–60° C. After 4 hours' heating a further 2 cm$^3$ isopropylisocyanate was added and the heating maintained from a further 3 hours.

After neutralizing the excess isocyanate with a little acetic acid the reaction medium was poured over about 1 liter of ice water.

The precipitate was filtered off and vacuum dried. The crude reaction product comprised the desired product and the dicondensation product.

The two products were isolated using silica gel chromatography (eluent: CH$_2$Cl$_2$—MeOH—NH$_4$OH). 6.2 g of N-(6-piperidino-2-amino-3-oxide-4-pyrimidinyl),N'-isopropylurea was obtained as white crystals melting at 224°–225° C.

| Elemental Analysis: C$_{13}$H$_{22}$N$_6$O$_2$ | | | | |
|---|---|---|---|---|
| | C % | H % | N % | O % |
| Calculated: | 53.04 | 7.53 | 28.55 | 10.87 |
| Found: | 52.50 | 7.56 | 28.31 | 11.38 |

1.75 g of N,N''-(6-piperidino-3-oxide-2,4-pyrimidinyl)-bis-(N'-isopropyl)urea, the dicondensation product, was obtained as white crystals melting at 208°–209° C. after recrystallization from methanol.

| Elemental Analysis: C$_{17}$H$_{29}$N$_7$O$_3$ | | | | |
|---|---|---|---|---|
| | C % | H % | N % | O % |
| Calculated: | 53.80 | 7.70 | 25.85 | 12.65 |
| Found: | 53.77 | 7.73 | 25.88 | 12.80 |

EXAMPLE VII

Synthesis of N-(6-piperidino-4-amino-3-oxide-2-pyrimidinyl),N'-cyclo hexylurea

Stage 1

Synthesis of
N-(4-amino-6-hydroxy-2-pyrimidinyl),N'-cyclohexylurea

A solution of 10 cm$^3$ of cyclohexylisocyanate in 50 cm$^3$ of N-methylpyrrolidone was added dropwise to a suspension of 10 g of 2,4-diaminopyrimidine-6-hydroxy pyrimidinyl in about 100 cm$^3$ of N-methylpyrrolidone at 60° C. Following addition the temperature was maintained for 3 hours. An additional 2 cm$^3$ of cyclohexyliso cyanate was added and the temperature raised to 90° C. for 2 hours. After verifying by TLC that the starting compound had completely disappeared, a mixture of 5 cm$^3$ of acetic acid in 20 cm$^3$ of water as added and the reaction medium left overnight at room temperature.

The solution was poured over 1 liter of water and agitated for about 1 hour. The desired product was filtered and 17 g of a white powder recovered after drying, which powder had a capillary melting point of 236° C.

| Elemental Analysis: C$_{11}$H$_{17}$N$_5$O$_2$ | | | | |
|---|---|---|---|---|
| | C % | H % | N % | O % |
| Calculated: | 52.57 | 6.82 | 27.87 | 12.73 |
| Found: | 51.85 | 6.75 | 27.53 | 12.55 |

Stage 2

Synthesis of N-(6-paratoluyloxysulfonyl-4-amino-2-pryimidinyl),N'-cyclohexylurea A solution of 1N soda was added to a suspension of 8 g of N-(4-amino-6-hydroxy-2-pyrimidinyl),N'-cyclohexylurea and 12.2 g of paratoluenesulfonyl chloride in a mixture of 120 cm$^3$ of water and 40 cm$^3$ acetone at 40° C. The reaction was followed by continuously monitoring the pH of the reaction medium to ensure that the soda added was rapidly consumed.

When the reaction had finished, TLC was used to verify that all the starting product had disappeared. A further 100 cm$^3$ of dilute soda was added to eliminate the excess of paratoluenesulfonyl chloride.

The precipitate thus obtained was filtered and washed with plenty of water (until the washings were neutral).

After drying 8.3 g of pure product melting at 203°-205° C. was recovered.

| Elemental Analysis: $C_{18}H_{23}N_5O_4S$ | | | | |
|---|---|---|---|---|
| C % | H % | N % | O % | S % |
| Calculated: 53.32 | 5.72 | 17.78 | 15.78 | 7.91 |
| Found: 53.11 | 5.65 | 17.31 | 15.63 | 7.88 |

Stage 3

Synthesis of N-(6-paratoluyloxysulfonyl-4-amino-3-oxide-2-pyrimidinyl),N'-cyclohexylurea 20 cm$^3$ of formic acid and 6 cm$^3$ of 110 vol oxygenated water were added to a suspension of 3 g of N-(paratoluyloxysulfonyl-4-amino-2-pyrimidinyl),N'-cyclo hexylurea in 100 cm$^3$ dioxan. The reaction medium was brought to 55° C. and maintained thereat for about 1 hour (the starting compound went into solution). A further 3 cm$^3$ of 110 vol oxygenated water was added and the temperature maintained for a further hour.

The reaction medium was poured over 300 cm$^3$ of ice water and the precipitate formed was filtered and washed with plenty of water.

After drying, a white powder was recovered whose $^1$H NMR, 80 MHz spectrum agreed with the expected structure and whose melting point was 215° C. (the product started to turn brown after 130° C.).

Stage 4

Synthesis of N-(6-piperidino-4-amino-3-oxide-2-pyrimidinyl),N'-cyclo hexylurea 0.5 cm$^3$ of piperidine was added to a solution of 1.5 g of N-(6-paratoluyloxysulfonyl-4-amino-3-oxide-2-pyrimidinyl),N'-cyclohexylurea in 50 cm$^3$ of THF. The reaction medium was agitated for ½ hour at room temperature, then heated to 60° C. for 1 hour.

At the end of the reaction the medium was poured into water and the product extracted with ethyl acetate.

The crude reaction product was purified using silica gel chromatography (eluent: CH$_2$Cl$_2$—MeOH). 750 mg of a pink-tinged white powder melting at 183°-185° C. was recovered whose $^1$H NMR, 80 MHz spectrum agreed with the expected structure.

EXAMPLE VIII

A further synthesis of N-(6-piperidino-4-amino-3-oxide-4-pyrimidinyl),N'-cyclo hexylurea 30 cm$^3$ of an aqueous 10N potash solution was added to a solution of 1 g of bis-N,N''-(6-piperidino-3-oxide-2,4-pyrimidinyl),N'-cyclohexylurea in 50 cm$^3$ of isopropanol. The reaction medium was maintained at 80° C. for 4 hours.

After verifying that the starting compound had totally disappeared, the isopropanol was evaporated off and the residue taken up into 100 cm$^3$ of water.

The desired product was extracted with ethyl acetate, the organic phase was washed with plenty of water, then dried over magnesium sulfate.

After evaporating off the solvent 500 mg of a white product was obtained which recrystallized from a methanol-water mixture and had a melting point of 180°-182° C.

EXAMPLE IX

Synthesis of N-(6-piperidino-4-amino-3-oxide-2-pyrimidine),N'-n-butyl urea

Stage 1

Synthesis of N-(4-amino-6-hydroxy-2-pyrimidinyl),N'-n-butylurea 24.6 cm$^3$ of n-butylisocyanate was added all at once to a suspension of 25 g of 2,4-diamino-6-hydroxy pyrimidine in about 200 cm$^3$ of N-methylpyrrolidone at 60° C. The reaction is exothermic and the temperature rose to 100° C. The temperature was maintained at 80° C. for 1 hour, whereupon the solution was clear yellow and TLC indicated that the starting compound had completely disappeared.

The reaction medium was left to cool to room temperature and 20 cm$^3$ acetic acid in 50 cm ethanol was added to neutralize the excess of n-butylisocyanate.

The solution was then poured over 1.5 liter of ice water, agitated for 30 minutes and the precipitate filtered off.

After drying, 40.4 g of white crystals having a melting point of 226° C. were recovered. The $^1$H NMR, 80 MHz spectrum agreed with the expected structure.

| Elemental Analysis: $C_9H_{15}N_5O_2$ | | | |
|---|---|---|---|
| C % | H % | N % | O % |
| Calculated: 47.99 | 6.71 | 31.09 | 14.21 |
| Found: 47.54 | 6.65 | 29.75 | 14.04 |

Stage 2

Synthesis of N-(6-paratoluyloxysulfonyl-4-amino-2-pyrimidinyl),N'-n-butylurea A solution of 1N of soda was added dropwise to a suspension of 30 g of N-(4-amino-6-hydroxy-2-pyrimidinyl),N'-n-butylurea and 50.7 g paratoluene sulfonyl chloride in a mixture of 600 cm$^3$ of water and 180 cm$^3$ of acetone at 40° C.

The reaction was followed by monitoring the pH of the reaction medium to ensure that the added soda was rapidly consumed.

When the reaction had finished, TLC was used to verify that the starting compound had completely disappeared, then a further 200 cm³ of dilute soda was added to neutralize the excess paratoluenesulfonyl chloride.

The precipitate thus obtained was filtered and washed with plenty of water (until the washings were neutral).

After drying, 40.5 g of a faintly yellowish product was obtained which melted at 195°–197° C. and whose ¹H NMR, 80 MHz spectrum agreed with the expected structure.

EXAMPLE X

Synthesis of N-(6-piperidino-4-amino-3-oxide-2-pyrimidinyl),N'-n-butylurea 12 g of potash was added in small quantities to a boiling, agitated solution of 50 g of bis-N,N''-(6-piperidino-3-oxide-2,4-pyrimidinyl),N'-n-butylurea in 1.2 l of ethanol. Once all the potash had dissolved, the reaction medium was maintained at a temperature between 70° C. and 80° C. for 5 hours. Transformation of the diurea into a monourea was monitored using TLC. Once complete, the ethanol was eliminated by vacuum evaporation. The product was then agitated in 250 cm³ of water and after filtration and drying, 36 g of a beige solid was obtained.

After recrystallizing twice from ethanol, 25 g of N-(6-piperidino-4-amino-3-oxide-2-pyrimidinyl),N'-n-butylurea was isolated as white crystals with a melting point of 208° C.

The product was analyzed in its hydrated form.

| Elemental Analysis: $C_{14}H_{24}N_6O_2 \cdot H_2O$ | | | | |
|---|---|---|---|---|
| | C % | H % | N % | O % |
| Calculated: | 53.74 | 7.89 | 26.86 | 11.51 |
| Found: | 53.74 | 7.95 | 26.83 | 11.48 |

EXAMPLE XI

Synthesis of N-(6-morpholino-2-amino-3-oxide-4-pyrimidinyl),N'-n-butylurea 20 cm³ of morpholine was added to a suspension of 10 g of N-(2-amino-3-oxide-6-chloro-4-pyrimidinyl), N'-n-butylurea (prepared according to example V) in 100 cm³ of ethanol. The reaction medium was maintained at 50° C. for 4 hours, then the alcohol evaporated off. The residue was recrystallized twice from acetonitrile. 6.5 g of a white product melting at 185°–186° C. was obtained.

By treating the hydrochloride form of this product with an aqueous sodium bicarbonate solution in heterogeneous phase, 4 g of a white powder melting at 168°–170° C. was obtained whose ¹H NMR, 80 MHz spectrum agreed with the expected structure.

EXAMPLE XII

Preparation of N-(6-pyrrolidino-2-amino-3-oxide-4-pyrimidinyl),N'-n-butylurea and of N,N''-(6-pyrrolidino-3-oxide-2,4-pyrimidinyl) bis-(N'-n-butyl)urea 3.3 cm³ of butylisocyanate was added dropwise to a suspension of 4 g of 6-pyrrolidino-2,4-diamino pyrimidine-3-oxide in 40 cm³ of anhydrous DMSO, agitated at 60° C. under an inert atmosphere. 3 hours later, since the starting compound had not been completely transformed, a further 0.5 cm³ of butylisocyanate was added and the temperature brought to 90° C. and maintained thereat for 3 further hours. The temperature was then reduced to 40° C. and the mixture was poured over 300 cm³ of ice water. The precipitate formed was extracted twice using 100 cm³ of ethyl acetate, the organic phase was washed with water, dried over sodium sulfate and the solvent eliminated by vacuum evaporation. The monourea-diurea mixture was dissolved in a minimum of methanol, then put onto a silica gel column. Eluting the column with methylene chloride, then with a methylene chloride-methanol mixture produced fractions containing one of the products in a pure form. After evaporating these fractions, 2 g of N-(6-pyrrolidino-2-amino-3-oxide-4-pyrimidinyl),N'-n-butylurea was isolated which on recrystallization from ethyl acetate produced white crystals having a melting point of 191° C.

| Elemental Analysis: $C_{13}H_{22}N_6O_2$ | | | | |
|---|---|---|---|---|
| | C % | H % | N % | O % |
| Calculated: | 53.04 | 7.53 | 28.55 | 10.87 |
| Found: | 52.66 | 7.52 | 28.29 | 10.57 |

0.75 g of N,N''-(6-pyrrolidino-3-oxide-2,4-pyrimidinyl)-bis-(N'-n-butyl)urea was also isolated, recrystallized from methanol.

| Elemental Analysis: $C_{18}H_{31}N_7O_3$ | | | | |
|---|---|---|---|---|
| | C % | H % | N % | O % |
| Calculated: | 54.94 | 7.94 | 24.92 | 12.20 |
| Found: | 54.84 | 7.88 | 24.91 | 12.38 |

COMPOSITION EXAMPLES

1) A lotion having the following composition was prepared:

| | |
|---|---|
| N-(6-piperidino-2-amino-3-oxide-4-pyrimidinyl), N'-n-butylurea | 5 g |
| Propylene glycol | 20 g |
| Ethanol | 50 g |
| Water   qsp | 100 g |

2) A lotion intended to stimulate hair regrowth was prepared having the following composition:

| | |
|---|---|
| N-(6-piperidino-2-amino-3-oxide-4-pyrimidinyl), N'-cyclohexylurea | 3 g |
| Propylene glycol | 20 g |
| Ethanol | 50 g |
| Water   qsp | 100 g |

1 to 2 ml of these lotions were applied to the areas of alopecia on the scalp. These applications, along with an optional massage to encourage penetration, were made once or twice a day.

3) The following gel composition was prepared:

| | |
|---|---|
| N-(6-piperidino-2-amino-3-oxide-4-pyrimidinyl), N'-n-isopropylurea | 2 g |
| Propylene glycol | 3 g |

-continued

| | |
|---|---|
| Ethanol | 50 g |
| Preservative qs | |
| Water qsp | 100 g |

4) The following gel composition was prepared:

| | |
|---|---|
| N-(6-piperidino-4-amino-3-oxide-2-pyrimidinyl), N'-n-butylurea | 3 g |
| Methylhydroxypropylcellulose, sold by DOW CHEMICAL under the trade name "METHOCEL F" | 1 g |
| Ethanol | 40 g |
| Water qsp | 100 g |

5) A lotion having the following composition was prepared:

| | |
|---|---|
| N-(6-morpholino-2-amino-3-oxide-4-pyrimidinyl), N'-n-butylurea | 5 g |
| Propylene glycol, monomethylether | 30 g |
| Ethanol | 40 g |
| Water qsp | 100 g |

We claim:

1. A cosmetic composition for stimulating the growth of hair, comprising, in a cosmetically acceptable support, a cosmetically effective concentration of at least one compound of formula (I):

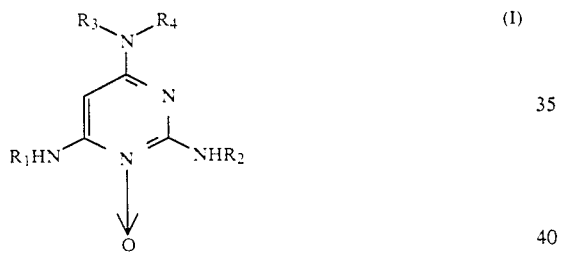

tautomeric forms of the compounds of formula (I), which have the formulae:

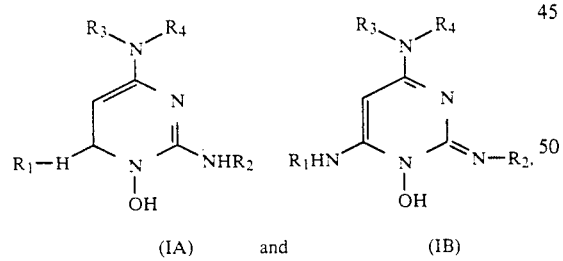

and salts esters and amides of the compounds of formula (I), wherein:

$R_3$ and $R_4$ are either
(i) identical of different and are selected from the group consisting of hydrogen atoms, linear or branched $C_1$-$C_{18}$ alkyl groups, alkenyl groups having 2 to 18 carbon atoms, cycloalkyl groups having 5 to 8 carbon atoms which may have one or more substituents selected from the group consisting of a lower alkyl groups, alkenyl groups and cycloalkyl groups, wherein said alkenyl and cycloalkyl groups may have one or more substituent hydroxyl groups,
(ii) an aryl group or an aralkyl group having the general formula:

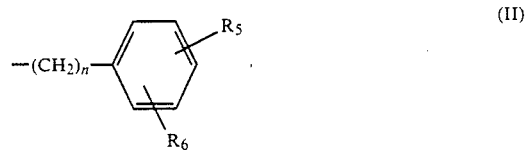

in which n is 0 to 4, and $R_5$ and $R_6$, which may be identical or different, are selected from the group consisting of hydrogen atoms, $C_1$ to $C_6$ lower alkyl groups, nitro groups, hydroxyl groups, alkoxy groups, halogen atoms, carboxyl groups, and the salts, esters, or amides of any of the preceding groups, or
(iii) together with the nitrogen atom to which they are each linked, form a heterocyclic group selected from the group consisting of morpholino, piperidino, pyrrolidino, piperazino, and 4'-N-alkylpiperazino;

$R_1$ and $R_2$ are selected from the group consisting of hydrogen atoms and carbamoyl groups having the formula:

in which $R_1$ and $R_2$ may be identical or different but are not both hydrogen, $R_7$ is selected from the group consisting of linear or branched $C_1$ to $C_{18}$ alkyl groups, $C_2$ to $C_{18}$ alkenyl groups, $C_5$ to $C_8$ cycloalkyl groups, and aryl or aralkyl groups that have formula (II); and said concentration is effective for stimulating the growth of hair.

2. The composition of claim 1, wherein the composition is in the form of a lotion, gel soap or shampoo and said effective concentration is between 0.01 and 5% by weight in a physiologically acceptable support.

3. The composition of claim 1, further comprising hydrating agents, antiseborrheic agents, hair growth agents, other than those of formula (I), steroid or nonsteroid anti-inflammatory agents, carotenoids, eicosa-5,8,11,14-tetraynoic acid, eicosa-5,8,11-triynoic acid and esters and amides of eicosa-5,8,11,14-tetraynoic acid, eicosa-5,8,11-triynoic acid.

4. The composition of claim 1, further comprising preservatives, stabilizers, pH regulators, osmotic pressure modifiers, emulsifiers, UV-A and UV-B filters or antioxidizing agents.

5. A process for the cosmetic treatment of the hair, comprising applying an effective amount of at least one cosmetic composition of claim 1 to the scalp, wherein said amount is sufficient to stimulate the growth of hair.

* * * * *